US010174360B2

(12) United States Patent
Borges et al.

(10) Patent No.: US 10,174,360 B2
(45) Date of Patent: Jan. 8, 2019

(54) METHODS FOR ANALYZING GLYCAN-DERIVED MONOSACCHARIDES

(71) Applicant: Arizona Board of Regents, for and on behalf of, Arizona State University, Scottsdale, AZ (US)

(72) Inventors: Chad Borges, Avondale, AZ (US); Douglas Rehder, Phoenix, AZ (US)

(73) Assignee: ARIZONA BOARD OF REGENTS, FOR AND ON BEHALF OF, ARIZONA STATE UNIVERSITY, Scottsdale, AZ (US)

( * ) Notice: Subject to any disclaimer, the term of this patent is extended or adjusted under 35 U.S.C. 154(b) by 223 days.

(21) Appl. No.: 14/394,021

(22) PCT Filed: Mar. 14, 2013

(86) PCT No.: PCT/US2013/031804
§ 371 (c)(1),
(2) Date: Oct. 10, 2014

(87) PCT Pub. No.: WO2013/154751
PCT Pub. Date: Oct. 17, 2013

(65) Prior Publication Data
US 2015/0376679 A1 Dec. 31, 2015

Related U.S. Application Data

(60) Provisional application No. 61/622,159, filed on Apr. 10, 2012.

(51) Int. Cl.
*C12Q 1/48* (2006.01)
*C12Q 1/54* (2006.01)
*G01N 33/66* (2006.01)

(52) U.S. Cl.
CPC .............. *C12Q 1/48* (2013.01); *C12Q 1/54* (2013.01); *G01N 33/66* (2013.01);
(Continued)

(58) Field of Classification Search
None
See application file for complete search history.

(56) References Cited

U.S. PATENT DOCUMENTS 6,649,780 B1  11/2003  Eibl et al.
2004/0147033 A1  7/2004  Zachary et al.
(Continued)

FOREIGN PATENT DOCUMENTS

WO  WO/2009/117666  9/2009

OTHER PUBLICATIONS

Borges, C.R., et al., "Multiplexed Surrogate Analysis of Glycotransferase Activity in Whole Biospecimens", In Analytical Chemistry, vol. 85, No. 5, Mar. 2013, pp. 2927-2936.
(Continued)

*Primary Examiner* — Jennifer Pitrak McDonald
*Assistant Examiner* — Qing Xu
(74) *Attorney, Agent, or Firm* — Byrne Poh LLP; Nina R. Horan

(57) ABSTRACT

The present disclosure provides a method for analyzing glycart-derived monosaccharides in a sample. The present disclosure also provides a method for detecting or monitoring a disease or disorder in a patient. In addition, the present disclosure provides a method of determining aberrant glycotransferase activity. The present disclosure further provides a system for analyzing or comparing glycates in a sample.

10 Claims, 4 Drawing Sheets

(52) U.S. Cl.
CPC ..... *G01N 2400/10* (2013.01); *G01N 2400/38* (2013.01); *G01N 2560/00* (2013.01); *G01N 2800/102* (2013.01); *G01N 2800/104* (2013.01); *G01N 2800/285* (2013.01); *G01N 2800/7028* (2013.01); *G01N 2800/7071* (2013.01)

(56) References Cited

U.S. PATENT DOCUMENTS

| | | | |
|---|---|---|---|
| 2005/0014718 A1 | 1/2005 | Natunen et al. | |
| 2006/0120961 A1 | 6/2006 | Schneider et al. | |
| 2009/0324617 A1* | 12/2009 | Satomaa ............ | A61K 39/0011 424/174.1 |
| 2010/0144553 A1 | 6/2010 | Bosques et al. | |
| 2011/0118390 A1 | 5/2011 | Feron et al. | |
| 2011/0135689 A1 | 6/2011 | Apicella et al. | |
| 2011/0300173 A1 | 12/2011 | Guerry et al. | |

OTHER PUBLICATIONS

Goetz, J.A., et al., "Enzymatic/Chemical Release of O-Glycans Allowing MS Analysis at High Sensitivity", In Analytical Chemistry, vol. 81, Dec. 2009, pp. 9546-9552.

Heiss, C., et al., "The structure of Cryptococcus neoformans galactoxylomannan contains beta-D-glucuronic acid", in Carbohydrate Research, vol. 344, No. 7, 2009, pp. 9546-9552.

Higgins, E., "Carbohydrate analysis throughout the development of a protein therapeutic", In Glycoconjugate Journal, vol. 27, Nov. 2009, pp. 211-225.

Hoffman, R.M., "Prostate-specific antigen testing accuracy in community practice", In BMC Family Practice, vol. 3, No. 19, Oct. 2002, pp. 1-8.

International Preliminary Report on Patentability dated Oct. 23, 2014 in International Patent Application No. PCT/US2013/031804.

International Search Report dated Jun. 4, 2013 in International Patent Application No. PCT/US2013/031804.

Issallovic, D., et al. "Profiling of human serum glycans associated with liver cancer and cirrhosis by IMS-MS", In Journal of Proteome Research, vol. 344, No. 7, 2009, pp. 915-920.

Mills, K., et al., "Synthesis of novel internal standards for the quantitative determination of plasma ceramide trihexoside in Fabry disease by tandem mass spectrometry", In FEBS Letters, vol. 515, Mar. 2002, pp. 171-176.

Morelle, W., et al., "Mass spectrometric approach for screening modifications of total serum N-glycome in human diseases: application to cirrhosis", In Glycobiology, vol. 16, No. 4, Dec. 2005, pp. 281-293.

Rohlfing, C.L., et al., "Use of GHb (HbA1 c) in Screening for Undiagnosed Diabetes in the U.S. Population", In Diabetes Care, vol. 23, No. 2, Feb. 2000, pp. 187-191.

Salto, T., et al., "Composition of free form glycopeptides isolated from bovien colostrum", In International Dairy Journal, vol. 3, No. 2, 1993, pp. 129-139.

Thompson, I.M., "Operating Characteristics of Prostate-Specific Antigen in Men With an Initial PSA Level of 3.0 ng/mL or Lower", In Journal of the American Medial Association, vol. 294, No. 1, Jul. 6, 2005, pp. 66-71.

Touboul, D., et al., "Fast fingerprinting by MALDI-TOF mass spectrometry of urinary sediment glycosphingolipids in Fabry disease", In Analytical and Bioanalytical Chemistry, vol. 382, No. 5, Jul. 2005, pp. 1209-1216.

Written Opinion of the International Search Authority dated Jun. 4, 2013 in International Patent Application No. PCT/US2013/031804.

* cited by examiner

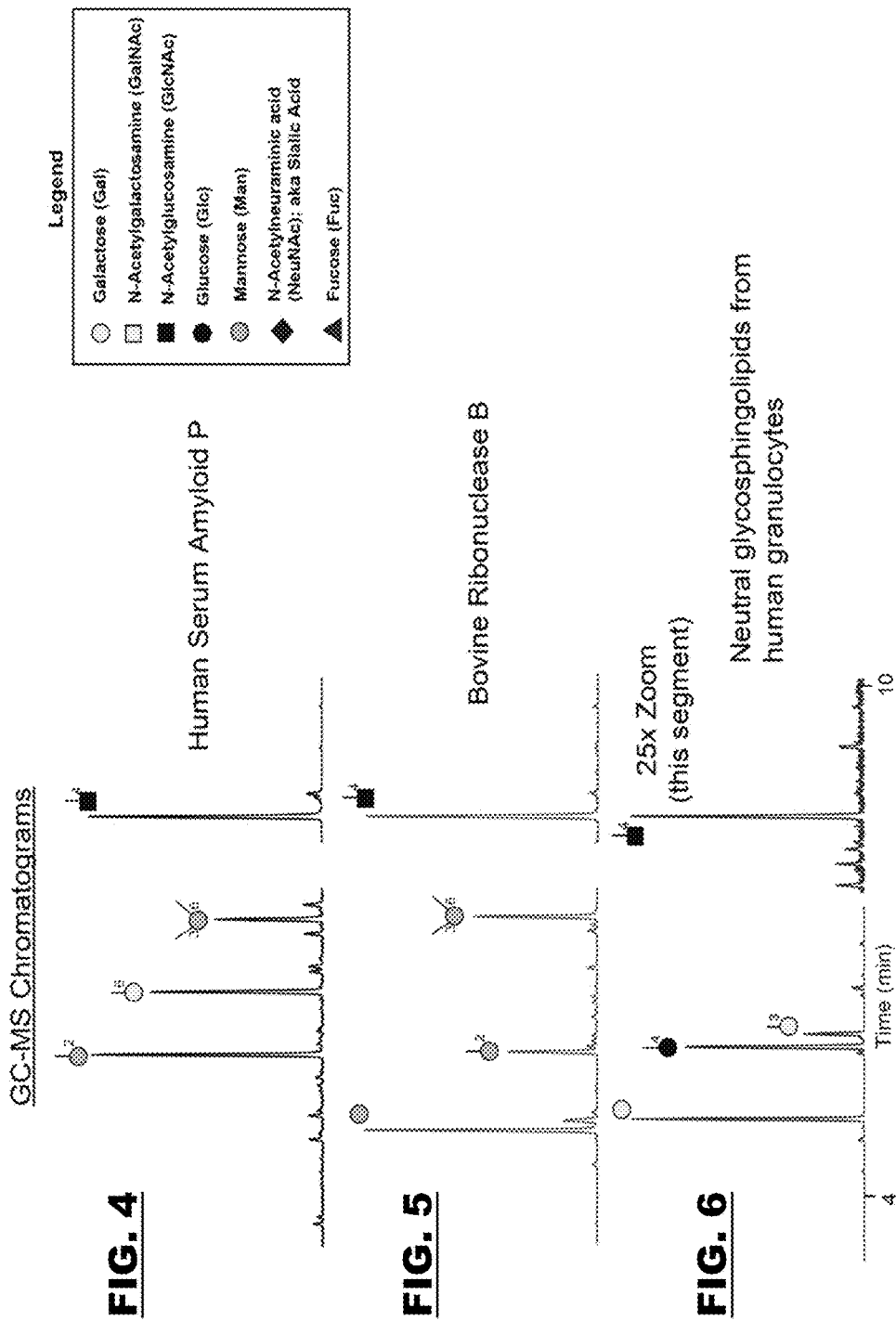

US 10,174,360 B2

METHODS FOR ANALYZING GLYCAN-DERIVED MONOSACCHARIDES

CROSS REFERENCE TO RELATED APPLICATION

This application is a national stage application under 35 U.S.C. § 371 of International Application No. PCT/US2013/031804, filed Mar. 14, 2013, which claims the benefit under 35 U.S.C. § 119(e) of U.S. Provisional Application No. 61/622,159, filed Apr. 10, 2012, the contents of all of which are incorporated by reference herein in their entirety.

FIELD OF THE INVENTION

The present disclosure provides a method for analyzing glycan-derived monosaccharides in a sample. The present disclosure also provides a method for detecting or monitoring a disease or disorder in a patient. In addition, the present disclosure provides a method of determining aberrant glycotransferase activity. The present disclosure further provides a system for analyzing or comparing glycans in a sample.

BACKGROUND OF THE INVENTION

Glycans are complex, heterogenous biological sugar polymers generally found attached to protein or lipids and are displayed on cell and macromolecular surfaces. Glycans are created in the endoplasmic reticulum and golgi apparatus organelles by enzymes known as glycotransferases. The molecular structure of glycans strongly affects the biological activity of the protein or lipid to which it is attached. Aberrant glycotransferase activity (which, in turn, produces aberrant glycan structures) is a well-known hallmark of essentially every known type of cancer.

The altered expression of a single glycotransferase can result in the production of a complex, heterogeneous mixture of n unique, abnormal whole-glycan structures rather than in an uniformly increase expression of a single whole-glycan structure (FIG. 1). These heterogeneous mixtures of whole-glycan structures are often very difficult to fully characterize. Thus, existing cancer biomarkers that are based on intact glycan structure are generally based on one or a few particular aberrant glycan structures (out of n) or perhaps as set of very closely related aberrant glycan structures that result in a unique antibody or lectin epitope.

One known method for characterizing glycans on the basis of molecular weight consists of permethylation, release from the protein substrate, and analysis intact by mass spectrometry. In this approach, a pre-isolated glycan or pre-isolated O-linked glycoprotein is permethylated, purified and analyzed intact by MALDI-mass spectrometry (MS) or liquid chromatography (LC)-electrospray ionization (ESI)-MS. Goetz et al. ("Enzymatic/Chemical Release of O-Glycans Allowing MS Analysis at High Sensitivity." *Anal. Chem.*, 2009, 81 (23), pp 9546-9552) describe this method. Importantly, Goetz et al. state that their method does not release N-linked glycans from proteins and they did not discuss glycolipids in this paper. The analysis of N-linked glycans by this approach would require preliminary cleavage from their protein substrates (usually by enzyme), followed by isolation then permethylation. Most notably, Goetz et al. describe their method as a means to analyze pre-isolated glycoproteins or glycans. They do not consider complex mixtures of glycoproteins, whole biofluids or tissues.

A second known method for characterizing pre-isolated glycans known as glycan methylation analysis was developed by the University of Georgia's Complex Carbohydrate Research Center (CCRC) [Heiss et al. ("The structure of *Cryptococcus neoformans* galactoxylomannan contains beta-D-glucuronic acid," *Carbohydrate Research* 2009, 344 (7), pp 915-20)]. This method is a trifluoroacetic acid (TFA)-based methylation analysis and consists of permethylation, hydrolysis, reduction and acetylation

SUMMARY OF THE INVENTION

The present disclosure provides a method for analyzing glycan-derived monosaccharides in a sample. The method comprises (a) permethylating a sample comprising glycans; (b) partially purifying the permethylated glycans; (c) hydrolyzing the permethylated glycans thereby forming permethylated monosaccharides; (d) reducing the permethylated monosaccharides thereby forming partially methylated alditols; (e) acetylating the partially methylated alditol thereby forming partially methylated alditol acetates; (f) partially purifying the partially methylated alditol acetates; and (g) analyzing partially methylated alditol acetates (PMAAs) using a substance identification procedure.

In some embodiments, the glycans comprise a member selected from the group consisting of N-linked glycans, glycolipids and O-linked glycans.

In some embodiments, step (a) includes an initial substep of mixing the sample comprising glycans with as labeled chemical substance. In some aspects of this embodiment, the labeled chemical substance is a monosaccharide selected from the group consisting of heavy, stable-isotope labeled glucose, heavy fucose, heavy xylose, heavy galactose, heavy mannose, heavy N-acetylglucosamine (GlcNAc), heavy N-acetylgalactosamine (GalNAc) and combinations thereof in other aspects, the labeled chemical substance is a polysaccharide comprising a saccharide selected from the group consisting of heavy, stable isotope labeled glucose, heavy fucose, heavy xylose, heavy galactose, heavy mannose, heavy N-acetylglucosamine GlcNAc), heavy N-acetylgalactosamine (GalNAc) and combinations thereof.

In some embodiments, step (b) comprises liquid/liquid extraction, in some aspects of this embodiment, step (b) comprises adding a solution of NaCl followed by a halogenated organic solvent. In some aspects, the halogenated solvent is chloroform.

In some embodiments, step (d) uses a reducing agent selected from the group consisting of $NaBH_4$, $NaBD_4$ and a combination thereof.

In some embodiments, step (f) comprises liquid/liquid extraction.

In some embodiments, analyzing partially methylated alditol acetates detects an increased or decreased concentration of glycan nodes.

In some embodiments, the glycan nodes comprise monosaccharide-and-linkage-specific glycan chain links exhibiting molecular surrogacy for glycotransferase activity. In some aspects, the glycan nodes comprise glycan monosaccharides selected from the group consisting of terminal fucose, 3-linked fucose, terminal xylose, 2-linked xylose, 4-linked xylose, terminal glucose, terminal mannose, terminal galactose, 2-linked glucose, 3-linked glucose, 2-linked mannose, 4-linked galactose, 4-linked mannose, 4-linked glucose, 3-linked mannose, 2-linked galactose, 3-linked galactose, 6-linked glucose, 6-linked mannose, 6-linked galactose, 3,4-linked galactose, 3,4-linked glucose, 2,4-linked glucose, 3,6-linked glucose, 2,3,4-linked glucose, 3,4,6-linked glucose, 3,4,6-linked galactose, 2,3-linked galactose, 2,4-linked mannose, 4,6-linked glucose, 2,6-linked mannose, 3,6-linked mannose, galactose, 3,4,6-linked mannose, terminal GlcNAc, terminal GalNAc, 4-linked GlcNAc, 3-linked GlcNAc, 3-linked GalNAc, 6-linked GlcNAc, 3,4-linked GlcNAc, 4-linked GalNAc, 6-linked GalNAc, 4,6-linked GlcNAc, 3,6-linked GalNAc.

In some embodiments, step (a) includes the substep of initially removing one or more of compounds selected from the group consisting of glycolipid, N-linked glycans and O-linked glycans.

In some embodiments, step (e) comprises pre-saturating an acetic anhydride reagent with water prior to adding it to the partially methylated alditol.

The present disclosure also provides a method for detecting or monitoring a disease or disorder in a patient. The method comprises (a) obtaining a sample comprising glycans from a patient; (b) permethylating the glycans; (c) partially purifying the permethylated glycans; (d) hydrolyzing the permethylated glycans thereby forming permethylated monosaccharides; (e) reducing the permethylated monosaccharides thereby forming partially methylated alditols; (f) acetylating the partially methylated alditol thereby forming partially methylated alditol acetates; and (g) detecting the altered presence of glycan nodes; wherein the altered presence of glycans nodes is associated with a disease or a disorder.

In some embodiments, the disease or disorder is cancer. In other embodiments, the disease or disorder is a glycan affective disease. In some embodiments, the disease or disorder is an immunological disorder.

In embodiments in which the disease or disorder is cancer, the cancer is selected front the group consisting of ovarian cancer, prostate cancer, pancreatic cancer, liver cancer, multiple myeloma, breast cancer, lung cancer, gastric cancer, thyroid cancer and colorectal cancer.

In embodiments in which the disease or disorder is an immunological disorder, the immunological disease is selected from the group consisting of rheumatoid arthritis, lupus and multiple sclerosis.

In some embodiments, step (b) includes the initial substep of mixing the sample with a labeled chemical substance.

In some embodiments, step (g) comprises using a substance identification procedure.

In some embodiments, the glycan nodes comprise a monosaccharide-and-linkage-specific glycan chain links exhibiting surrogacy for glycotransferase activity.

In some embodiments, the glycan nodes comprise glycan monosaccharides selected from the group consisting of terminal fucose, 3-linked fucose, terminal xylose, 2-linked xylose, 4-linked xylose, terminal glucose, terminal mannose, terminal galactose, 2-linked glucose, 3-linked glucose, 2-linked mannose, 4-linked galactose, 4-linked mannose, 4-linked glucose, 3-linked mannose, 2-linked galactose, 3-linked galactose, 6-linked glucose, 6-linked mannose, 6-linked galactose, 3,4-linked galactose, 3,4-linked glucose, 2,4-linked glucose, 3,6-linked glucose, 2,3,4-linked glucose, 3,4,6-linked glucose, 3,4,6-linked galactose, 2,3-linked galactose, 2,4-linked mannose 4,6-linked glucose, 2,6-linked mannose, 3,6-linked mannose, 3,6-linked galactose, 3,4,6-linked mannose, terminal GlcNAc, terminal GalNAc, 4-linked GlcNAc, 3-linked GlcNAc, 3-linked GalNAc, 6-linked GlcNAc, 3,4-linked GlcNAc, 4-linked GalNAc, 6-linked GalNAc, 4,6-linked GlcNAc, 3,6-linked GalNAc.

In some embodiments, the glycans comprise a member selected from the group consisting of N-linked glycans, glycolipids and O-linked glycans.

The present disclosure also provides a method of determining aberrant glycotransferase activity. The method comprises (a) permethylating the glycans; (b) partially purifying the permethylated glycans; (c) hydrolyzing the permethylated glycans thereby forming permethylated monosaccharides; (d) reducing the permethylated monosaccharides thereby forming partially methylated alditols; (e) acetylating the partially methylated alditol thereby forming partially methylated alditol acetates; (f) partially purifying the partially methylated alditol acetates; and (g) comparing the profile of the partially methylated alditol acetates (PMAAs) with a control profile to determine aberrant glycotransferase activity.

In some embodiments, step (a) includes the initial substep of mixing the sample comprising glycans with a labeled chemical substance.

The present disclosure also provides a system for analyzing or comparing glycans in a sample. The system comprises (a) a database, tangibly embodied in a non-transitory computer-readable medium; and (b) a feature extractor adapted to access the database and compare values therein with those from the sample, so that datasets are generated and pattern analysis or data mining is performed to generate or analyze glycans nodes within the database and those from the sample. The database, contains information descriptive of glycans nodes. This information is obtained by (i) optionally mixing as sample comprising glycans with a labeled chemical substance; (ii) permethylating the glycans; (iii) partially purifying the permethylated glycans; (iv) hydrolyzing the permethylated glycans thereby forming permethylated monosaccharides; (v) reducing the permethylated monosaccharides thereby forming partially methylated alditols; (vi) acetylating the partially methylated alditol thereby forming partially methylated alditol acetates; (vii) partially purifying the partially methylated alditol acetates; and (viii) analyzing partially methylated alditol acetates (PMAAs) using a substance identification procedure.

In some embodiments of the methods described above, the sample can be selected from the group consisting of blood plasma, serum, seminal fluid, prostatic fluid, other human biological fluid and combinations thereof.

In some embodiments of the methods described above, the labeled chemical substance can be selected from the group consisting of an internal standard, a heavy-isotope labeled glycan polymer(s), heavy-isotope labeled monosaccharides, heavy glucose, heavy fucose and heavy GlcNAc. In other embodiments, the labeled chemical substance is a polysaccharide comprising a saccharide selected from the group consisting of heavy, stable isotope labeled glucose, heavy fucose, heavy xylose, heavy galactose, heavy mannose, heavy N-acetylglucosamine (GlcNAc), heavy N-acetylgalactosamine (GalNAc) and combinations thereof.

In some embodiments of the methods described above, the substance identification procedure is selected from the group consisting of gas chromatography-mass spectrometry, mass spectrometry, liquid chromatography-mass spectrometry, liquid chromatography, gas chromatography, flame ionization detector, and combinations thereof.

BRIEF DESCRIPTION OF THE FIGURES

FIG. 4 shows a GC-MS chromatogram of a sample comprising prepurified Human Serum amyloid P, which contains only N-linked glycans and no O-linked glycans.

FIG. 5 shows a GC-MS chromatogram of a sample comprising pre-purified Bovine Ribonuclease B (RNase B), which contains only one N-glycan per protein molecule and no O-linked glycans.

FIG. 6 shows a GC-MS chromatogram of a sample comprising pre-purified glycolipids from human granulocytes.

Figure 1:
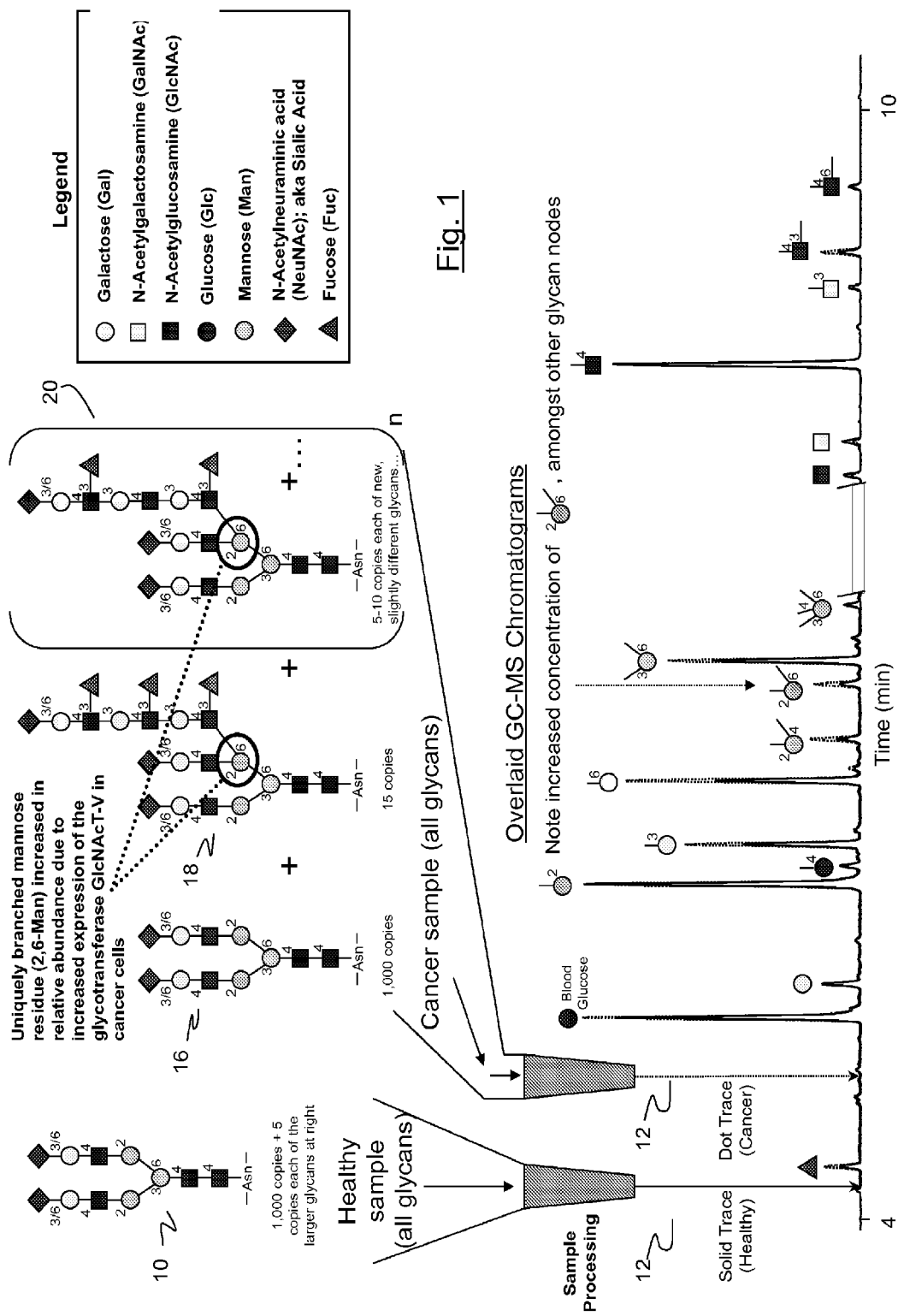
FIG. 1 shows a conceptual overview of a method for analyzing glycan-derived monosaccharides in a sample according to an embodiment of this disclosure.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE INVENTION

In order that the invention herein described may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

Methods for Analyzing, Glycan-Derived Monosaccharides

The present invention provides a method for analyzing glycan-derived monosaccharides in a sample. This method provides, for the first time, an analysis of O-linked protein glycans, N-linked protein glycans and glycolipids.

The method comprises the steps of (a) permethylating a sample comprising glycans; (b) partially purifying the permethylated glycans; (c) hydrolyzing the permethylated glycans thereby forming permethylated monosaccharides; (d) reducing the permethylated monosaccharides thereby forming partially methylated alditols; (e) acetylating the partially methylated alditol thereby forming partially methylated alditol acetates; (f) partially purifying the partially methylated alditol acetates; and (g) analyzing partially methylated alditol acetates (PMAAs) using a substance identification procedure.

Samples used in the methods of this disclosure may be obtained from a patient. As used herein, the term "patient" means an animal, preferably a mammal, and most preferably, a mouse, rat, other rodent, rabbit, dog, cat, swine, cattle, sheep, horse, or primate, and even more preferably a human.

The sample may be blood, plasma, serum, seminal fluid, prostatic fluid, tissue, other biofluid optionally derived from tissue ex vivo or combinations thereof. In some embodiments, the sample is derived from a diseased organ, tissue or secretion therefrom. Samples derived from a diseased organ or tissue include, but are not limited to sputum, prostatic fluid or semen, lung tissue, breast tissue, liver tissue, colon tissue and prostate tissue.

The samples used in the methods of this disclosure comprise glycans. In some embodiments, the glycans comprise one or more members selected from the group consisting N-linked glycans, glycolipids and O-linked glycans.

In step (a) of the method for analyzing glycan-derived monosaccharides in a sample, the sample comprising glycans is permethylated. Permethylation can be carried out according to methods known in the art. In some embodiments, permethylation comprises mixing the sample with a base and a methyl halide. The base can be sodium hydroxide and the methyl halide can be iodomethane.

In some embodiments, permethylation is performed, over solid phase sodium hydroxide. The permethylating mixture can be allowed to sit on the beads with occasional mixing. This embodiment simplifies processing samples in batches.

In some embodiments, step (a) includes an initial substep of mixing the sample comprising glycans with a labeled chemical substance. The labeled chemical substance can be a monosaccharide selected from the group consisting of heavy, stable-isotope labeled glucose, heavy fucose, heavy xylose, heavy galactose, heavy mannose, heavy N-acetylglucosamine (GlcNAc), heavy N-acetylgalactosamine (GalNAc) and combinations thereof. Alternatively, the labeled chemical substance is a polysaccharide comprising a saccharide selected from the group consisting of heavy, stable isotope labeled glucose, heavy fucose, heavy xylose, heavy galactose, heavy mannose, heavy N-acetylglucosamine (GlcNAc), heavy N-acetylgalactosamine (GalNAc) and combinations thereof. The labeled chemical substance can be added for purposes of quantification.

In some embodiments, step (a) includes the substep of initially removing one or more of compounds selected from the group consisting of glycolipid, N-linked glycans and O-linked glycans. Pre-isolation of glycolipid, N-linked glycans and O-linked glycans may be desirable in diagnostic applications. When the glycolipid is removed, it can be removed by liquid/liquid extraction using methods known in the art. See, Mills et al., "Synthesis of novel internal standards for the quantitative determination of plasma ceramide trihexoside in Fabry disease by tandem mass spectrometry," *FEBS Lett* 515 (1-3), pp 171-6, When N-linked glycans or O-linked glycans are removed, they can be removed by enzymatic treatment or chemical methods, respectively, using methods known in the art. See, e.g., Higgins, "Carbohydrate analysis throughout the development of a protein therapeutic," *Glycoconj J* 27 (2), pp 211-25.

In step (b) of the method for analyzing glycan-derived monosaccharides in a sample, the permethylated glycans are partially purified. As used herein, the term "partially purifying permethylated glycans" refers to methods of at least partially removing permethylated glycans from a mixture of other compounds.

In some embodiments, partially purifying permethylated glycans comprises liquid/liquid extraction. With liquid/liquid extraction, the partially purified permethylated glycans is in the organic phase. In some embodiments, the liquid/liquid extraction is repeated until the organic phase is clear.

Liquid/liquid extraction, in some embodiments, comprises adding a solution of NaCl followed by a halogenated organic solvent. The halogenated organic solvent can be methylene chloride or chloroform. Adding the solution of NaCl prior to the halogenated organic solvent reduces the number of liquid/liquid extractions steps needed to partially purify the permethylated glycans. This reduces the amount of solvent used in the liquid/liquid extraction and saves a significant amount of sample processing time.

In step (c) of the method for analyzing glycan-derived monosaccharides in a sample, the permethylated glycans are hydrolyzed to form permethylated monosaccharides. The permethylated glycans can be hydrolyzed according to any method known in the art. In some embodiments, the permethylated glycans are hydrolyzed by acid. In some embodiments, the acid can be trifluoroacetic acid.

In step (d) of the method for analyzing glycan-derived monosaccharides in a sample, the permethylated monosaccharides are reduced to partially methylated alditols. The reducing agent used in this step can be any known in the art. In some embodiments, the reducing agent selected from the group consisting of $NaBH_4$, $NaBD_4$ and a combination thereof.

In step (e) of the method for analyzing glycan-derived monosaccharides in a sample, the partially methylated alditols are acetylated thereby forming partially methylated alditol acetates. The acetylation step can be performed using any known acetylating reagent. In some embodiments, the acetylating, reagent is acetic anhydride.

In some embodiments, step (e) comprises pre-saturating an acetic anhydride reagent with water prior to adding it to the partially methylated alditol. In some embodiments, the acetic anhydride reagent is acetic anhydride. This embodiment can improve the yield and consistency of yield of HexNAc residues (e.g., N-acetylglucosamines and N-acetylgalactosamines.

In step (f) of the method for analyzing glycan-derived monosaccharides in a sample, the partially methylated alditol acetates are partially purified. Step (f) is performed in the same way as described above for step (b).

In step (g) of the method for analyzing glycan-derived monosaccharides in a sample, the partially methylated alditol acetates (PMAAs) are analyzed using a substance identification procedure.

The substance identification procedure used in the methods of this disclosure can be selected from the group consisting of gas chromatography-mass spectrometry, mass spectrometry, liquid chromatography-mass spectrometry, liquid chromatography, gas chromatography, flame ionization detector, and combinations thereof.

In some embodiments, the analysis detects an increased or decreased concentration of glycan nodes. As used herein, the term "glycan nodes" refers to monosaccharide-and-linkage specific glycan polymer chain links and branch points. If the glycan polymer chain links and branch points are broken down and quantified from the pool of all glycan structures in a sample, these glycan nodes can represent molecular surrogates of aberrant glycotransferase activity. Thus, in some embodiments, the glycan nodes comprise monosaccharide-and-linkage-specific glycan chain links exhibiting molecular surrogacy for glycotransferase activity.

In some embodiments, the glycan nodes comprise glycan monosaccharides selected from the group consisting of terminal fucose, fucose, terminal xylose, 2-linked xylose, 4-linked xylose, terminal glucose, terminal mannose, terminal galactose, 2-linked glucose, 3-linked glucose, 2-linked mannose, 4-linked galactose, 4-linked mannose, 4-linked glucose, 3-linked mannose, 2-linked galactose, 3-linked galactose, 6-linked glucose, 6-linked mannose, 6-linked galactose, 3,4-linked galactose, 3,4-linked glucose, 2,4-linked glucose, 3,6-linked glucose, 2,3,4-linked glucose, 3,4,6-linked glucose, 3,4,6-linked galactose, 2,3-linked galactose, 2,4-linked mannose, 4,6-linked glucose, 2,6-linked mannose, 3,6-linked mannose, 3,6-linked galactose, 3,4,6-linked mannose, terminal GlcNAc, terminal GalNAc, 4-linked GlcNAc, 3-linked GlcNAc, 3-linked GalNAc, 6-linked GlcNAc, 3,4-linked GlcNAc, 4-linked GalNAc, 6-linked GalNAc, 4,6-linked GlcNAc, 3,6-linked GalNAc.

In some embodiments, the steps following permethylation are carried out using silanized glassware to improve recovery.

Advantageously, in the present method, there are no special sample handling required. The molecular targets of the present method are stable to conventional biological sample collection techniques and conventional long-term storage conditions. This is not the case with other analytical technologies that are based on the analysis of RNA or the measurement of enzyme activity.

Figure 2:
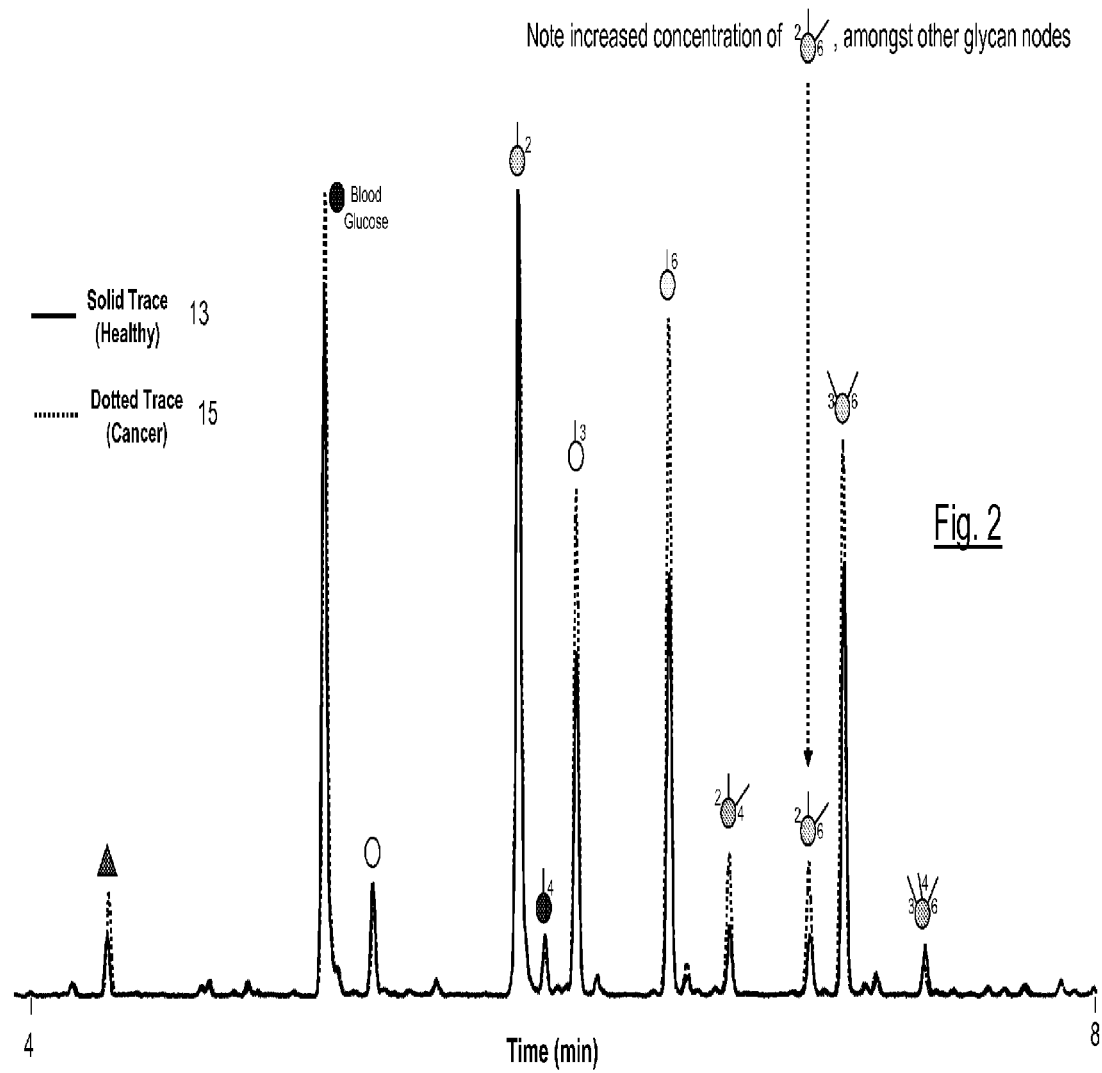
FIG. 2 shows an expanded view overlaid GC-MS chromatogram of FIG. 1.
Figure 3:
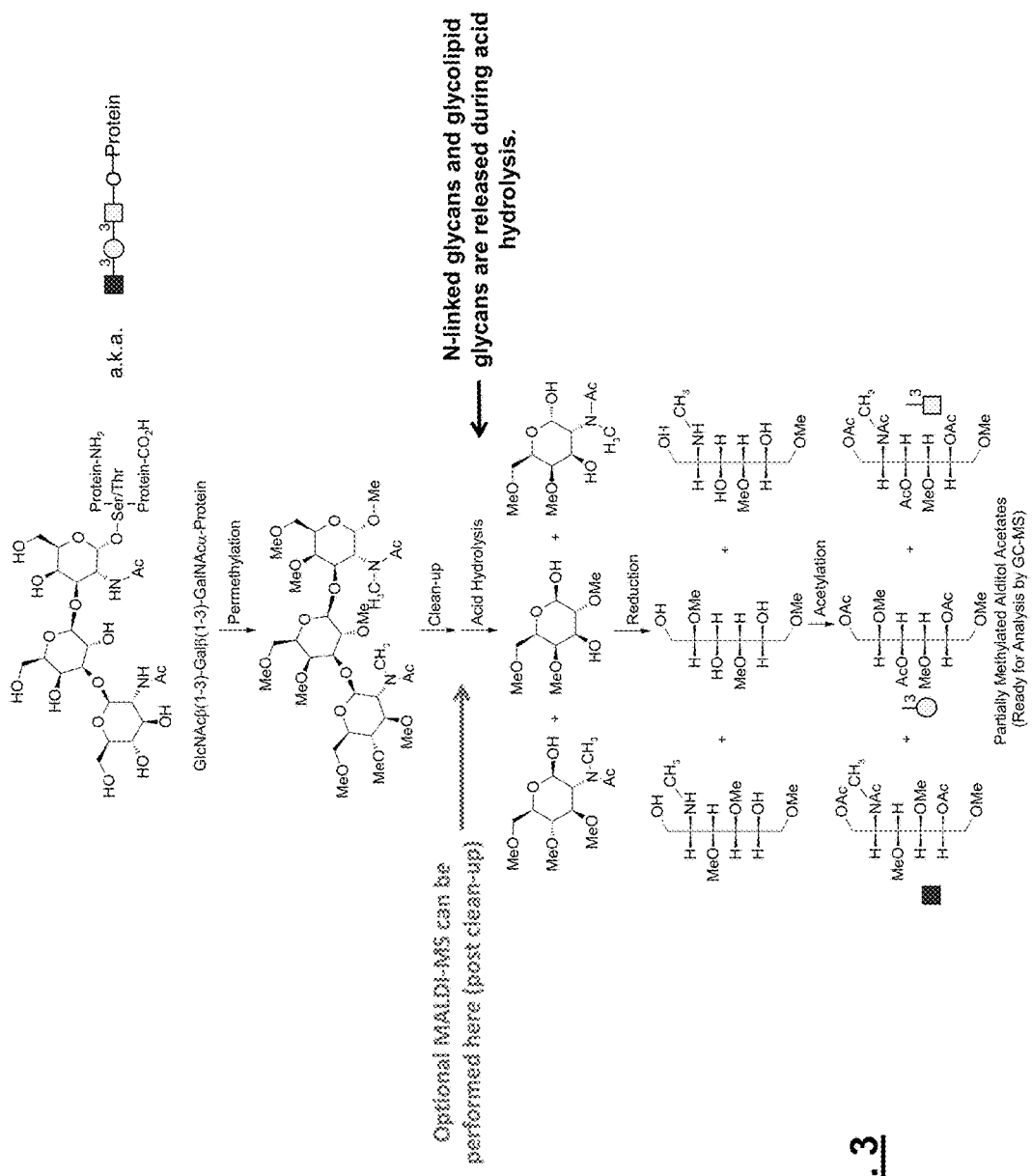
FIG. 3 schematically illustrates a method for analyzing glycan-derived monosaccharides in a sample according to an embodiment of this disclosure.

FIGS. 1-3 illustrate a method of analyzing glycan-derived monosaccharides in a sample according to an embodiment of the invention. As shown in FIG. 3, the method comprises (a) obtaining a sample comprising glycans 310 and optionally adding a labeled chemical substance; (b) permethylating the glycans 320; (c) partially purifying the permethylated glycans by liquid/liquid (L/L) extraction 325; (d) hydrolyzing the permethylated glycans in 2 M TFA at 120° C. to producing permethylated monosaccharides 330; (e) reducing the permethylated monosaccharides with NaBH4 (or NaBD4) to create partially methylated alditols 340; and (f) acetylating 350 the partially methylated alditols to form partially methylated alditol acetates 360; (g) partially purifying the partially methylated alditol acetates; and (h) analyzing the partially methylated alditol acetates (PMAAs) by GC-MS.

FIG. 1 provides a conceptual overview of the method of analyzing glycan-derived monosaccharides. By way of example, healthy sample 10 comprises 1,000 copies+5 copies each of larger glycans. Healthy sample 10 is processed in processing step 12 as shown in FIG. 3. When analyzed using GC-MS techniques, the healthy samples generate (in part) the trace best shown in FIG. 2, as solid trace 13. As noted in FIG. 1, uniquely branched mannose residue (2,6-Man) increased in relative abundance due to increased expression of the glycotransferase GlcNAcT-V in cancer cells.

As illustrated, upregulated glycotransferases (e.g., Glc-NAcT-V as highlighted here) cause increases in the quantity of specific uniquely linked glycan monosaccharide residues (glycan "nodes"). The glycan nodes can lead to formation of a mixture of heterogenous glycan structures at low copy number—each of which can be difficult to detect and quantify consistently. But when the glycan nodes are pooled together analytically from amongst all the aberrant glycan structures their combined numbers add up to produce larger-than-normal gas chromatography-mass spectrometry (GC-MS) peaks (actual chromatograms 100 shown in FIG. 1 and FIG. 2, for example). Numbers adjacent to monosaccharide residues in glycan structures indicate the position at which the higher residue is linked to the lower residue. (All residues link downward via their 1-position.) Since no cellulose is employed during sample processing, 4-Glc is derived mostly from glycosphingolipids. 3-GalNAc comes predominately from O-linked glycans.

Cancer samples 16, 18, and 20 containing 1,000 copies each of larger glycans (16), 15 copies of glycans (18) and 5-10 copies each of new slightly different glycans (20), were run through the process step 12. When analyzed using GC-MS techniques, the cancerous samples generate the dotted line trace best shown (in part) in FIG. 2, as dotted line trace 15.

Referring now specifically to FIG. 2, an expanded view overlaid GC-MS chromatogram of FIG. 1 is shown. Note the increased concentration of 2,6-linked mannose, amongst other glycan nodes.

FIGS. 4-6 illustrate the use of samples comprising different glycans. FIG. 4 shows a GC-MS chromatogram of a sample comprising N-linked glycans. The sample shown in FIG. 4 is a prepurified Human Serum Amyloid P (SAP), which bears only N-linked glycan. The data shown are consistent with the known subtype of SAP N-linked glycan, namely a "complex"-type N-linked glycan.

FIG. 5 shows a GC-MS chromatogram of a sample comprising only N-linked glycan and no O-linked glycans. The same shown in FIG. 5 is pre-purified Bovine Ribonuclease B (RNase B). As with SAP, the data shown for RNase B in FIG. 5 are consistent with the known subtype of RNase B N-linked glycan, namely "high mannose"-type N-linked glycan.

FIG. 6 shows a GC-MS chromatogram of a sample comprising glycolipids. The sample shown is pre-purified glycolipids from human granulocytes. Notably, FIGS. 4-6 are consistent with known glycan structures; Serum amyloid P carries a complex-type N-linked glycan; RNAse B carries predominately high mannose-type glycans; and neolacto-type glycosphingolipids from human blood are largely characterized by their lactose (Gal1-4Glc)-base, 3-Gal and 4-GlcNAc-containing structures.

Methods for Detecting or Monitoring a Disease or Disorder

The present disclosure also provides a method for detecting or monitoring a disease or disorder in a patient. The method comprises (a) obtaining a sample comprising glycans from a patient; (b) permethylating the glycans; (c) partially purifying the permethylated glycans; (d) hydrolyzing the permethylated glycans thereby forming permethylated monosaccharides; (e) reducing the permethylated monosaccharides thereby forming partially methylated alditols; (f) acetylating the partially methylated alditol thereby forming partially methylated alditol acetates; and (g) detecting, the altered presence of glycan nodes; wherein the altered presence of glycans nodes is associated with a disease or a disorder.

As used herein, the term "disease or disorder" refers to any disease or disorder in which glycotransferase activity has become disregulated. Such diseases or disorders include, but are not limited to, cancer, immunological and inflammation related diseases.

In some embodiments, the disease or disorder is cancer. In other embodiments, the disease or disorder is a glycan affective disease. In some embodiments, the disease or disorder is an immunological disorder.

In embodiments in which the disease or disorder is cancer, the cancer is selected from the group consisting of ovarian cancer, prostate cancer, pancreatic cancer, liver cancer, multiple myeloma, breast cancer, lung cancer, gastric cancer, thyroid cancer and colorectal cancer.

Immunological disorders include, but are not limited to, Autoimmune disorder selected from the group consisting of Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgi, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura Herpes gestationis Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, juvenile arthritis, Juvenile diabetes (Type I diabetes), Juvenile myositis, Kawasaki syndrome, Lambert-Eaton syndrome, Leukocytoclastic vasculitis, lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myosins, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatic, Polymyositis, Poster infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type I diabetes, Ulcerative colitis, Undifferentiated connective tissue disease (UCTD), Uveitis, Vasculitis, Vesiculobullous dermatosis, Vitiligo, and Wegener's granulomatosis (now termed Granulomatosis with Polyangiitis (GPA).

In some embodiments in which the disease or disorder is an immunological disorder, the immunological disease is selected from the group consisting of rheumatoid arthritis, lupus and multiple sclerosis.

Steps (a)-(g) of the method for detecting, or monitoring a disease or disorder are as described above for the method for analyzing glycans-derived monosaccharides.

In some embodiments, the method uses a sample of secretions or tissues derived directly from putative cancerous organs (e.g., sputum, prostatic fluid, lung tissue, breast tissue, liver tissue, colon tissue and prostate tissue etc), Advantageously, such samples are not diluted by glycans produced by other healthy organs. Thus, this embodiment can provide an early and accurate diagnosis of cancer. In addition, when applied to fluids or homogenized tissues, this embodiment may aid pathologists in making more objective diagnoses, decreasing their reliance upon more subjective forms of tissue staining and visualization under the microscope.

Methods of Determining Aberrant Glycotransferase Activity

The present disclosure also provides a method of determining aberrant glycotransferase activity. The method comprises (a) permethylating the glycans; (b) partially purifying the permethylated glycans; (c) hydrolyzing the permethylated glycans thereby forming permethylated monosaccharides; (d) reducing the permethylated monosaccharides thereby forming partially methylated alditols; (e) acetylating the partially methylated alditol thereby forming partially methylated alditol acetates; (f) partially purifying the partially methylated alditol acetates; and (g) comparing the profile of the partially methylated alditol acetates (PMAAs) with a control profile to determine aberrant glycotransferase activity.

Steps (a)-(g) are as described above in the methods for analyzing glycans-derived monosaccharides in a sample.

The profile of the PMAAs comprises glycan nodes. Glycan nodes represent some of the best possible molecular surrogates of glycotransferase activity because they provide a means by which to pool together into a simple, single molecular entity the glycan structural heterogeneity that inevitably results as a byproduct of a branching or extending glycotransferase activity. In other words, glycomic approaches that study unique individual whole glycan structures are focusing on individual fractional components from amongst possible dozens of (n) glycan structures which, as a composite, make up the sum total downstream molecular signature of an aberrant glycotransferase. But in this conventional approach, because the signal from the aberrant glycotransferase is often split out into n unique, highly complex glycans, it is nearly impossible to identify as well as consistently and routinely quantify each unique, highly complex glycan structure that corresponds to a single disregulated glycotransferase. Analyzing the glycan nodes as described herein provides about 1:1 (rather than 1/n:1) molecular surrogate for an aberrant glycotransferase (FIG. 1).

System for Analyzing or Comparing Glycans in a Sample

The present disclosure also provides a system for analyzing or comparing glycans in a sample. The system comprises (a) a database, tangibly embodied in a non-transitory computer-readable medium; and (b) a feature extractor adapted to access the database and compare values therein with those from the sample, so that datasets are generated and pattern analysis or data mining is performed to generate or analyze glycans nodes within the database and those from the sample. The database, contains in formation descriptive of glycans nodes. This information is obtained, by (i) optionally mixing a sample comprising glycans with a labeled chemical substance; (ii) permethylating the glycans; (iii) partially purifying the permethylated glycans; (iv) hydrolyzing the permethylated glycans thereby forming permethylated monosaccharides; (v) reducing the permethylated monosaccharides thereby forming partially methylated alditols; (vi) acetylating the partially methylated alditol thereby forming partially methylated alditol acetates; (vii) partially purifying the partially methylated alditol acetates; and (viii) analyzing partially methylated alditol acetates (PMAAs) using a substance identification procedure.

Step (i) through (vii) are as described above in the methods for analyzing glycans-derived monosaccharides.

In order that this invention be more fully understood, the following examples are set forth. These examples are for the purpose of illustration only and are not to be construed as limiting the scope of the invention in any way.

EXAMPLES

Example 1—Glycolipid Pre-Extraction Protocol

The following example describes how to pre-isolate glycolipids from a sample. Theoretically, the targeted analysis of glycolipids (glycosphingolipids in particular) may be of significant diagnostic utility in certain cancer/biofluid-or-tissue combinations.

Aliquot 100 uL of biofluid or tissue sample and transfer to a 13×100 mm glass tube. (For the sample containing added glycolipids, pre-transfer and dry the glycolipids in the 13×100 mm glass tube, then add the aqueous albumin.) Add 2 mL of chloroform:methanol (2:1, v/v). Note: Do not let the tubes sit around at all at this stage before initiating vortex. Lay tubes down horizontally and shake/vortex/agitate for 20 minutes. Remove precipitated protein by centrifugation at 3000 g for 10 min. Transfer the organic layer to another tube and add 400 uL water. Shake vortex/agitate for another 20 minutes Centrifuge at 3000 g for 10 min. Split off ~10-15% of the lower (organic) layer to a new silanized autosampler vial and dry under nitrogen (for MALDI-MS of intact glycolipids).

Example 2—Analysis of Intact Glycolipids

MALDI-MS of Intact Glycolipids I) Reconstitute the glycolipids in 5 uL of chloroform:methanol (2:1, v/v) 2) On a stainless steel MALDI target, mix sample 1:1 with DHB matrix solution (10 mg/mL in 9:1 (v/v) acetone:methanol) and let dry. This procedure should reveal [M+Na]+ adducts. 3) For MS/MS if desired: On a separate spot, mix sample 1:1 with DHB matrix solution (10 mg/mL in 9:1 (v/v) acetone: methanol) and mix in 0.2 uL of 0.1 M LiCl in 9:1 acetone: methanol. This procedure should reveal [M+Li]+ adducts which are useful for MALDI-MS/MS.

Example 3—Permethylation and Partial Purification of Permethylated Glycans

To a 1.5 mL polypropylene test tube add 9 uL of a whole biofluid (e.g., blood plasma, serum, seminal fluid, etc.) or tissue sample to be analyzed. (If glycolipids have been pre-isolated and dried, simply add 9 uL of water at this stage.) Add 1 uL of a 10 mM stock solution of heavy-isotope labeled glucose as an internal standard (IS). (We employ D-glucose from Cambridge Isotope Laboratories which is labeled with deuterium at all protons attached to carbon and which is labeled with 13-C at every carbon atom.) Add 270 uL of dimethylsulfoxide (DMSO) (Quantification precision may be improved by adding the IS into a stock solution of DMSO, avoiding small-volume pipetting errors). Fill a 1-mL spin column (with a polyethylene frit—cellulose frits must be avoided) with sodium hydroxide beads to just under the first outer bevel and cover completely with acetonitrile. Spin for a few seconds at 5000 rpm in a microcentrifuge and discard the acetonitrile. Fill the spin column with DMSO, spin and discard the DMSO. Fill again with DMSO and plug the spin column. Add 105 uL of iodomethane using a gas tight syringe to avoid pipetting errors due to low liquid viscosity. (In total this is triple the recipe of Goetz) Spin the column to get rid of the DMSO in which it was briefly stored while preparing the sample. Apply the sample to the NaOH column. Let sit for 10-12 minutes with occasional stirring. [Alternatively, plug both the bottom and top of the column and slowly rotate end-over-end for the 10-12 minute incubation period. Spin the sample for 30 s at 4000 rpm to retrieve the glycan-containing liquid; place the liquid sample in silanized 13×100 glass test tube. Add 300 uL of acetonitrile to the spin column to wash off all of the permethylated glycan. Spin at 10,000 rpm for 30 s, collect the acetonitrile and pool it with the rest of the sample. (The NaOH beads in the spin column can now be discarded.) To the liquid sample add approximately 35 mL a 0.5 M NaCl (add first) and 1.2 mL of chloroform. Perform liquid/liquid extraction, saving the chloroform layer. This will need to be repeated a total of 3-4 times to get a clear chloroform layer.

Example 4—Optional Side Analysis

MALDI-MS of released permethylated, sodiated O-glycans: Split ~10% of the chloroform layer into a 600-uL eppendorf tube. Dry under nitrogen for analysis by MALDI-MS as follows: 1) Resuspend samples in 4 uL of ethanol. Sonicate if needed to ensure complete dissolution. 2) On a MALDI target, mix samples 1:1 with DHB matrix. This DHB matrix is prepared at 10 mg/mL in 1 mM sodium acetate. 3) Dry samples under vacuum once spotted. After splitting off a portion of the chloroform layer for analysis by MALDI-MS, dry samples under a gentle stream of nitrogen.

Example 5. Hydrolysis, Reduction and Acetylation

Add 20 drops of 2M TFA (325 uL) to each sample. Heat at 121° C. for 2 h. Dry down after heating. (Concentrated TFA=13.0 M) Reduction of sugar aldehydes: Prepare a fresh 10 mg/ml solution of sodium borohydride or sodium borodeuteride in 1 M ammonium hydroxide (Concentrated ammonium hydroxide 14.5 M). Add 10-15 drops of this solution to each sample. 15 drops=475 uL. Mix and leave for 1 h. Add 5 drops MeOH and dry down. Add 10 drops (125 uL) of 9:1:MeOH:Acetic Acid and dry down. Fully dry in a vacuum chamber, like a commercial FoodSaver® vacuum chamber, for at least 10-15 minutes before proceeding. Acetylation of nascent hydroxyl groups: Add 250 ul of acetic anhydride pre-saturated with water (16 uL water plus 234 uL acetic anhydride) to the sample tube and vortex well to dissolve the solid material as much as possible. (Note: Pre-mixing the acetic anhydride with water in this manner just prior to use dramatically increases the yield of HexNAc residues. Without this step the yield of fully acetylated HexNAc residues can be too low to be useful.) Add 230 ul conc. TFA to the sample. Incubate at 50° C. for 10 minutes. Add approx. 2 ml methylene chloride and mix well. Add approx. 2 mL water and mix well. Remove the aqueous (top) layer. Repeat liquid/liquid extraction in this way once more. Remove the organic (bottom) layer into a silanized autosampler vial. Evaporate the organic layer under nitrogen in a silanized autosampler vial and reconstitute in 5 drops of acetone for injection onto the GC-MS.

Example 6—Analysis

One useful instrument for GC-MS is a Waters-brand GC-Time-of-Flight (TOF)-MS. Traditional quadrupole-based mass analyzers are less sensitive than that instrument in "full scan" mode. However, given that samples used here are generally injected at an inlet split ratio of 50 or 100-to-1 (with most of the sample going to waste), it is anticipated that by lowering the injection split ratio the samples prepared by the above-described methodology will be easily analyzed with a less sensitive instrument. Alternatively, since pre-targeted molecules are being analyzed, a traditional quadrupole may be operated in selected ion monitoring (SIM) mode, providing comparable sensitivity to our GC-TOF-MS. Notably, traditional quadrupole-based GC-MS instruments, while less sensitive, have better linear dynamic range and therefore may possess something of an advantage. A library of EI-mass spectra for these analytes can be found at the following Internet address: http://www.ccrc.uga.edu/databases/index.php#. The top 2-3 most abundant and/or diagnostic fragment ions for each analyte are then summed (using a 0.15 Da extracted on chromatogram mass window) for quantification. Analysis is carried out in a traditional manner by integration of summed extracted ion chromatogram peak areas.

While particular materials, formulations, operational sequences, process parameters, and end products have been set forth to describe and exemplify this invention, they are not intended to be limiting. Rather, it should be noted by those ordinarily skilled, in the art that the written disclosures are exemplary only and that various other alternatives, adaptations, and modifications may be made within the scope of the present invention. Accordingly, the present invention is not limited to the specific embodiments illustrated herein, but is limited only by the following claims.

What is claimed is:

1. A method for detecting or monitoring a disease or disorder in a patient, comprising
   (a) obtaining a sample comprising glycans from a patient;
   (b) permethylating the glycans in the sample obtained from step (a) without pre-purifying the glycans;

(c) partially purifying the permethylated glycans from step (b);
(d) hydrolyzing the permethylated glycans thereby forming permethylated monosaccharides;
(e) reducing the permethylated monosaccharides thereby forming partially methylated alditols;
(f) acetylating the partially methylated alditol thereby forming partially methylated alditol acetates; and
(g) detecting an altered presence of glycan nodes wherein the altered presence of glycans nodes is associated with a disease or a disorder.

2. The method of claim 1, wherein the disease or disorder is cancer.

3. The method of claim 1, wherein the disease or disorder is a glycan affective disease.

4. The method of claim 1, wherein step (b) includes an initial substep of mixing the sample with a labeled chemical substance.

5. The method of claim 1, wherein step (g) comprises detecting the altered presence of the glycan node by performing a substance identification procedure selected from the group consisting of gas chromatography-mass spectrometry, mass spectrometry, liquid chromatography-mass spectrometry, liquid chromatography, gas chromatography, flame ionization detection, and combinations thereof.

6. The method of claim 1, wherein the glycan nodes comprise glycan monosaccharides selected from the group consisting of terminal fucose, 3-linked fucose, terminal xylose, 2-linked xylose, 4-linked xylose, terminal glucose, terminal mannose, terminal galactose, 2-linked glucose, 3-linked glucose, 2-linked mannose, 4-linked galactose, 4-linked mannose, 4-linked glucose, 3-linked mannose, 2-linked galactose, 3-linked galactose, 6-linked glucose, 6-linked mannose, 6-linked galactose, 3,4-linked galactose, 3,4-linked glucose, 2,4-linked glucose, 3,6-linked glucose, 2,3,4-linked glucose, 3,4,6-linked glucose, 3,4,6-linked galactose, 2,3-linked galactose, 2,4-linked mannose, 4,6-linked glucose, 2,6-linked mannose, 3,6-linked mannose, 3,6-linked galactose, 3,4,6-linked mannose, terminal GlcNAc, terminal GalNAc, 4-linked GlcNAc, 3-linked GlcNAc, 3-linked GalNAc, 6-linked GlcNAc, 3,4-linked GlcNAc, 4-linked GalNAc, 6-linked GalNAc, 4,6-linked GlcNAc, and 3,6-linked GalNAc.

7. The method of claim 1, wherein the glycan comprises N-linked glycans, glycolipids and O-linked glycans.

8. The method of claim 1, wherein the glycan comprises N-linked glycans.

9. The method of claim 1, wherein the glycan comprises O-linked glycans.

10. The method of claim 1, wherein the glycan comprises glycolipids.

* * * * *